United States Patent [19]

Cotarca et al.

[11] Patent Number: 5,670,661
[45] Date of Patent: Sep. 23, 1997

[54] PROCESS FOR PRODUCING LACTONES AND LACTONES OBTAINED WITH THIS PROCESS

[75] Inventors: Livius Cotarca, Cervignano Del Friuli; Roberto Bianchini, Udine, both of Italy

[73] Assignee: Industrie Chimiche Caffaro S.p.A., Milan, Italy

[21] Appl. No.: 556,990

[22] PCT Filed: Jun. 8, 1994

[86] PCT No.: PCT/EP94/01866

§ 371 Date: Apr. 16, 1996

§ 102(e) Date: Apr. 16, 1996

[87] PCT Pub. No.: WO94/29294

PCT Pub. Date: Dec. 22, 1994

[30] Foreign Application Priority Data

Jun. 15, 1993 [IT] Italy ................... MI93A1272

[51] Int. Cl.$^6$ ............... C07D 313/00; C07D 307/02
[52] U.S. Cl. ............... 549/266; 549/271; 549/272; 549/273; 549/292; 549/295; 549/322; 549/323; 549/324
[58] Field of Search ............... 549/266, 292, 549/295, 271, 272, 273, 322, 323, 324

[56] References Cited

U.S. PATENT DOCUMENTS 3,380,457  4/1968  Schumacher ............... 131/17
4,988,825  1/1991  Bove ............... 549/272

FOREIGN PATENT DOCUMENTS

| 0332802 | 9/1989 | European Pat. Off. . |
| 0548774 | 6/1993 | European Pat. Off. . |
| 4001189 | 1/1992 | Japan . |
| 5230048 | 9/1993 | Japan . |
| 1203752 | 9/1970 | United Kingdom . |
| 1219332 | 1/1971 | United Kingdom . |

OTHER PUBLICATIONS

Patent Abstracts of Japan, 17:689, Abstract no. C–1143, 1993.

WPI Database, Week 9207, Derwent Publications Ltd., AN 92–053946 (1992).

*Primary Examiner*—Amelia Owens
*Attorney, Agent, or Firm*—Coleman & Sudol

[57] ABSTRACT

The present invention relates to a process for producing lactones starting from cyclic ketones which comprises an oxidation reaction which is performed in the presence of an optionally substituted cycloaliphatic peracid or of an optionally substituted aliphatic peracid that is immiscible with water. The process allows to obtain high selectivity, does not entail the use of dangerous reagents, and allows excellent economic advantages.

14 Claims, No Drawings

PROCESS FOR PRODUCING LACTONES AND LACTONES OBTAINED WITH THIS PROCESS

The present invention relates to a process for producing lactones, particularly starting from cyclic lactones. The invention also relates to the lactones obtained with the process.

A process for oxidizing ketones, including cyclic ketones, by using permonosulfuric acid as oxidizing agent has been known since the last century as the Baeyer-Villiger reaction (A. Yon Baeyer and V. Villiger, Ber. 1899, 32, 3265; 1400, 33, 850). Other oxidizing agents have been used for this reaction, such as for example peracetic acid, described by R. Criegel (Liebig Annalen, 1948, 560, 127) and in British patent No. 1,203,752. In particular, peracetic acid entails problems, first of all due to the unavoidable co-production of acetic acid, which must in any case be isolated by separation from a high-boiling and thermally unstable product such as a lactone. Furthermore, peracetic acid is rather unstable and tends to decompose, thus creating problems in safety and reaction control. Finally, selectivity is unpredictable and generally rather low, in some cases around 25%.

The use of peracid salts such as magnesium permonophthalate (described in Syntesis 1015–1017, 1987) is also known; however, this salt requires an aqueous environment that entails a high level of lactone hydrolysis or persalts such as sodium perborate, described in U.S. Pat. No. 4,988,825, which requires a troublesome separation and recycling of boric acid.

The oxidizing agent most widely used is metachloroperbenzoic acid, described in Syntetic Comm 19, 829–833, 1989. In particular, metachloroperbenzoic acid requires rather diluted solutions, since otherwise it does not dissolve, and this entails larger reactor volumes and a very slow kinetics. Furthermore, subsequent purification is very onerous, since the solubilities of metachlorobenzoic acid, of metachloroperbenzoic acid and of the reaction products are rather similar, and therefore many successive crystallizations are required. The selectivity of the reaction is not very high anyway. Furthermore, metachloroperbenzoic acid requires an equimolar amount of trifluoroacetic acid (TFA), which is a highly expensive product with separation problems that are worsened by the poor thermal stability of TFA and of the reaction products; metachloroperbenzoic acid is scarcely reactive, indeed inert with certain ketone substrates and is industrially available with a 70% titer in a relatively impure form for chlorination by-products.

Finally, synthesis of lactones starting from cyclic ketones entails unpredictable regioselectivity and chemoselectivity.

EP-A-0 548 774 discloses a process for producing a lacton or an ester by the oxidation of ketones with oxygen in the presence of an aldehyde either in the absence of catalyst or in the presence of a heterogeneous iron-containing or ruthenium-containing catalyst. However the process cannot be said to be advantageous from the industrial point of view, because the used aldehyde is in very high amounts and is converted to the corresponding carboxylic acid which can be considered as a by-product.

JP-A-5 230 048 discloses a process for producing a lacton with 4–5 complicated passages, starting from raw material different from those of the field of the present invention.

EP-A-0 332 802 discloses only the use of an unsubstituted lacton, but does not disclose anything about its preparation.

JP-A-4 001 189 discloses the preparation of large-ring lactons for manufacturing of drugs, and useful high grade perfume, by oxidising large ring ketons in the presence of acqueous $H_2O_2$ and reciclable strong acidic cation exchange resins. However this process involves the use of high amount of resin which can also give rise to problems for its stability.

GB-A-1 219 332 discloses a process for the preparation of substituted gamma-butirrolactons, by acylation of an olefinic compound with manganese oxide. A large amount of manganese oxide must be used, with the co-production of many by-products, and with a very difficult separation.

U.S. Pat. No. 3 380 457 discloses a process for the preparation of saturated and unsaturated lactons with 6 carbon atoms (valerolactons) by cyclization of omega hydroxy acids, which are very expensive.

The aim of the present invention is therefore to overcome the drawbacks described above and to provide a reaction that can be performed in full safety without having to provide special safety systems.

An object is to achieve high selectivity.

Another object is to drastically simplify separation problems.

Another object is to provide a process which is economically highly advantageous.

Another object is to provide a reaction that can easily adapt to a large number of compounds.

This aim, these objects and others are achieved by the process according to the invention for preparing a compound with formula (1)

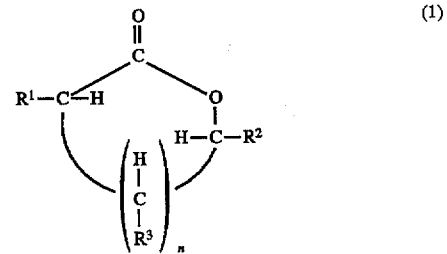

wherein each one of $R^1$, $R^2$, $R^3$ is: hydrogen, alkyl, alkyl aryl, halogen, cyano-alkyl, carboxy-alkyl, carbaalkoxy-alkyl or hydroxyl, and preferably is: —$CH_2$—$CH_2$—$R^4$, where $R^4$ is Y or a group that can be transformed into Y with known methods: Y is —COOH, —CN, $CONH_2$ or $COOR^5$; and $R^5$ is an optionally substituted alkyl or aryl radical; and n is between 1 and 9, said process comprising the oxidation of a compound with formula (2)

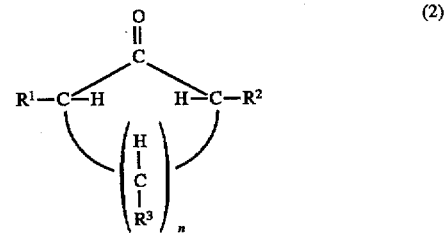

wherein $R^1$, $R^2$, $R^3$, and n have the same meaning, in the presence of an optionally substituted cycloaliphatic peracid, or of an optionally substituted aliphatic peracid that is immiscible with water.

The compound with formula (2) can be constituted for example by: 3-(2-cyclohexanonyl)propionitrile, 3-(2-cyclohexanonyl-propionic) acid, methyl-3-(2-cyclohexanonyl)propionate, butyl-3-(2-cyclohexanonyl) propionate.

Preferably, the cycloaliphatic peracid is formed by cyclohexane percarboxylic acid, optionally substituted in its cycloaliphatic ring. This peracid has the specific advantage that it can be obtained starting from cyclohexancarboxylic acid, which is a widely available, highly pure and low-cost product.

The compound with formula (1) can be recovered from the reaction mixture by extraction, crystallization, distillation, and preferably by film evaporation. In this case, the organic acid remains in solution and forms the residue of the originally introduced peracid. This organic acid can be reoxidized into a peracid and recycled.

The process can be performed in the presence of hydrogen peroxide. In this case, the water left over by hydrogen peroxide reduction is removed, the compound with formula (1) is recovered by extraction, and the organic acid and the unreacted compound with formula (2) are recycled.

Advantageously, the process is performed at a temperature between −25° C. and 150° C., preferably between 40° and 70° C. The process can furthermore be performed in a solution of an organic solvent chosen among: aliphatic or cycloaliphatic hydrocarbons with 5 to 10 carbon atoms, halogenated hydrocarbons, aromatic hydrocarbons, and aromatic and aliphatic esters, and is preferably chosen among petroleum ether, pentane, cyclopentane, cyclohexane, hexane and ethyl acetate.

Preferably, the molar ratio between the compound with formula (2) and the organic peracid is between 0.25 and 10, preferably between 0.8 and 1.2. The concentration by weight of the reagents in the solution can be between 1% and 100%, preferably between 15% and 40%.

Preferably, n is between 3 and 5, more preferably is 3.

According to a preferred embodiment of the invention, $R^1$ is hydrogen. In this case, the oxidation reaction surprisingly produces a compound with formula (3)

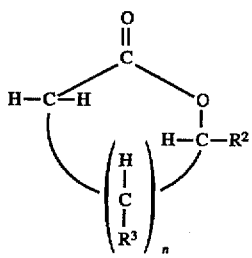
(3)

where $R^2$, $R^3$, and n have the above specified meaning.

The invention furthermore relates to the compound with formula

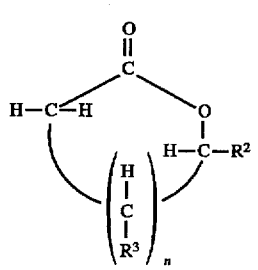
(3)

wherein $R^2$, $R^3$, and n have the above specified meaning, and to the compound with formula (4)

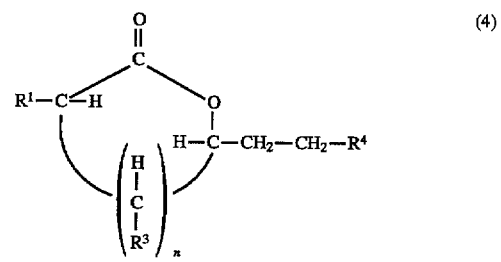
(4)

wherein $R^2$ is —$CH_2$—$CH_2$—$R^4$, $R^1$ and $R^3$ have the above specified meaning, and $R^4$ is Y or a group that can be transformed into Y with known methods: Y is —COOH, —CN, $CONH_2$ or $COOR^5$; and $R^5$ is an optionally substituted alkyl or aryl radical.

The following examples are enclosed by way of non-limitative example of the present invention.

EXAMPLE 1 according to the invention

7-cyanoethyl-2-oxepanone

A reactor is loaded with 500 g of 3-(2-cyclohexanonyl) propionitrile in 1000 ml of n-hexane; the reactor is heated to 50° C. and a solution of 520 g of perhexahydrobenzoic acid in 3000 ml of n-hexane is added. The reaction mixture is kept agitated for three hours at 55° C. and then the lower phase, mainly formed by 7-cyanoethyl-2-oxepanone and hexahydrobenzoic acid, is separated, whereas the upper phase contains hexahydrobenzoic acid and small amounts of unreacted 3-(2-cyclohexanonyl)propionitrile. Treatment of the lower phase with n-hexane allows to isolate 515 g of 7-cyanoethyl-2-oxepanone, equal to a yield of over 93% with 99% nitrile conversion. The 7-cyanoethyl-2-oxepanone (m.p. 35° C.) is identified by means of I.R. (KBr analytical techniques: 2970, 2870, 2245, 1720, 1175 $cm^{-1}$ and mass spectrometry by electron-impact ionization (70 eV): 168, 150, 139, 122, 113, 95, 84, 67, 55, 41. Analytically calculated values for $C_9H_{13}NO_2$ (167,21), C 64.65%, H 7.83%, N 8.38%. Found: C 64.51%, H 7.98%, N 8.46%.

Comparison example 2

7-cyanoethyl-2-oxepanone

A reactor is loaded with 151 g of 3-(2-cyclohexanonyl) propionitrile in 500 ml of n-hexane and 260 g of m-chloroperbenzoic acid (70% titer) dissolved at 50° C. in 2000 ml of n-hexane in 30 minutes. The solution is heated to 55° C. for 15 hours. Cooling separates from the solution, in crystalline form, part of the m-chlorobenzoic acid, which is scarcely soluble in the system, together with a heavy liquid phase which is formed by 7-cyanoethyl-2-oxepanone and by m-chlorobenzoic acid. 71.5 g of 7-cyanoethyl-2-oxepanone, impure with m-chlorobenzoic acid, are recovered from the lower phase. 24 g of 7-cyanoethyl-2-oxepanone are recovered from the upper phase by concentration and by several crystallizations. Conversion with respect to the initial ketone is 85%. Yield on the converted substance is 57%.

Comparison example 3

7-cyanoethyl-2-oxepanone

A reactor is loaded with 151 g of 3-(2-cyclohexanonyl) propionitrile in 500 ml of glacial acetic acid. 210 g of 40% peracetic acid are added to this solution in 2 hours, keeping the temperature between 30 and 40° C. Once addition has been completed, the reaction mixture is heated to 60° C. for 3 hours to complete the reaction. The reaction mixture is distilled in vacuum, recovering acetic acid and obtaining 150 g of an oily residue that contains 35% 7-cyanoethyl-2-oxepanone together with 65% by-products, with 98% conversion of the initial ketone (GLC analysis).

EXAMPLE 4

3.15 g of 2-methylcyclohexanone and 3.85 g of cyclohexane percarboxylic acid, dissolved in n-hexane, are kept at 50° C. for 3 hours under agitation. The reaction product is treated with $H_2O$, then neutralized with a solution of $Na_2CO_3$ and finally extracted with ethyl acetate. After solvent distillation, one obtains 3.3 g of 7-methyl-2-oxepanone, identified by mass spectrometry (EI, 70 eV), yielding the following m/e values: 128, 98, 80, 69, 55, 42.

EXAMPLE 5

3.3 g of 2-adamantanone and 2.9 g of cyclohexane percarboxylic acid dissolved in n-hexane are kept at 50° C. for 3 hours under agitation. The reaction product is treated with water, saturated $Na_2CO_3$ solution, and extracted with ethyl acetate. After solvent distillation one obtains 3.1 g of the corresponding lactone, which is identified by mass spectrometry (EI, 70 eV) yielding the following m/e values: 166, 149, 137, 122, 107, 93, 80, 67, 53, 41.

EXAMPLE 6

3.5 g of camphor and 3 g of cyclohexane percarboxylic acid dissolved in n-hexane are kept at 50° C. for 3 hours under agitation. The reaction product is treated with water, saturated $Na_2CO_3$ solution, and extracted with ethyl acetate. After solvent distillation one obtains 3.5 g of the corresponding lactone, identified by mass spectrometry (EI, 70 eV) yielding the following m/e values: 168, 153, 140, 126, 108, 93, 83, 69, 55, 43.

EXAMPLE 7

2 g of 2-methylcyclopentanone and 3 g of cyclohexane percarboxylic acid, dissolved in n-hexane, are heated at 50° C. for 3 hours under agitation. The reaction product is treated with water, saturated $Na_2CO_3$ solution, and extracted with ethyl acetate. After solvent distillation one obtains 2.2 g of the lactone, identified by mass spectrometry (EI, 70 eV) yielding the following m/e values: 114, 99, 70, 55, 42.

EXAMPLE 8

A reactor is loaded with 500 g of 3-(2-cyclohexanonyl) propionitrile, and a solution of 477 g of cyclohexane percarboxylic acid in 1450 g of cyclohexane carboxylic acid is added, keeping the reaction temperature at 50° C. for 3 hours. The reaction solvent is film-evaporated at low pressure, recovering 514 g of 7-cyanoethyl-2-oxepanone with a m.p. of 45° C., equal to a 93% yield.

We claim:

1. A process for preparing a compound according to formula (1):

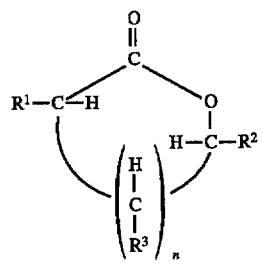

wherein each one of $R^1$ and $R^3$ is hydrogen, alkyl, alkyl-aryl, halogen, cyano-alkyl, carboxyl-alkyl, carbalkoxy-alkyl or hydroxy; and $R^2$ is hydrogen, alkyl, alkyl-aryl, halogen, cyano-alkyl, carboxy-alkyl, carbalkoxyalkyl, hydroxyl, or $CH_2CH_2$—$R^4$;

$R^4$ is Y or a chemical precursor of Y;

Y is COOH, CN, $CONH_2$ or $COOR^5$;

$R^5$ is alkyl, aryl or substituted alkyl or aryl; and n is between 1 and 9, said process comprising the oxidation of a compound according to formula (2):

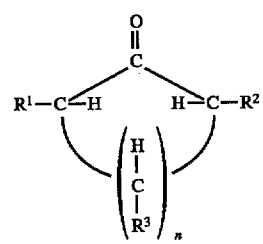

wherein each of $R^1$, $R^2$, $R^3$ and n have the same meaning as set forth above, said oxidation being conducted in the presence of an organic peracid selected from a cycloaliphatic peracid or substituted cycloaliphatic peracid, said peracid being substantially immiscible with water and being prepared by reoxidation of an organic acid coproduced in said oxidation.

2. A process for preparing a compound according to formula (1):

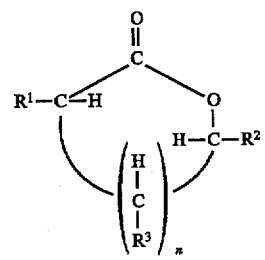

wherein each one of $R^1$ and $R^3$ is hydrogen, alkyl, alkyl-aryl, halogen, cyano-alkyl, carboxyl-alkyl, carbalkoxy-alkyl or hydroxy; and $R^2$ is hydrogen, alkyl, alkyl-aryl, halogen, cyano-alkyl, carboxy-alkyl, carbalkoxyalkyl, hydroxyl, or $CH_2CH_2$—$R^4$;

$R^4$ is Y or a chemical precursor of Y;

Y is COOH, CN, $CONH_2$ or $COOR^5$;

$R^5$ is alkyl, aryl or substituted alkyl or aryl; and n is between 1 and 9, said process comprising the oxidation of a compound according to formula (2):

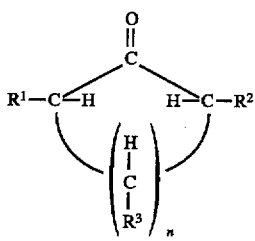

wherein each of $R^1$, $R^2$, $R^3$ and n have the same meaning as set forth above, said oxidation being conducted in the presence of a peracid selected from a cycloaliphatic peracid or substituted cycloaliphatic peracid, said peracid being substantially immiscible with water and being prepared by reoxidation of an organic acid coproduced in said oxidation, said compound according to formula (2) and said peracid being included in said oxidation process in a mole ratio between 0.25 and 10.

3. Process according to claim 1, wherein said compound with formula (2) is chosen among: 3-(2-cyclohexanonyl) propionitrile, methyl 3-(2-cyclohexanonyl) propionate, butyl 3-(2- cyclohexanonyl)propionate.

4. Process according to claim 1, wherein said cycloaliphatic peracid is cyclohexane percarboxylic acid, optionally substituted in its cycloaliphatic ring.

5. Process according to claim 1, wherein the compound with formula (1) is recovered by extraction, crystallization, distillation or film evaporation, from the reaction mixture, and an organic acid remains in solution and is reoxidized into peracid and recycled.

6. Process according to claim 1, wherein said process is performed in the presence of hydrogen peroxide in water.

7. Process according to claim 6, wherein the water is removed, the compound with formula (1) is recovered by extraction, and the organic acid and the compound with formula (2) that is unreacted are recycled.

8. Process according to claim 1, wherein said process is performed at a temperature between −25° C. and 150° C., preferably between 40° C. and 70° C.

9. Process according to claim 1, wherein said process is performed in a solution of an organic solvent chosen among: aliphatic hydrocarbons with 5 to 10 carbon atoms, halogenated hydrocarbons, aromatic hydrocarbons, and aliphatic and aromatic esters, and is preferably chosen between hexane, petroleum ether, pentane, cyclopentane, cyclohexane and ethyl acetate.

10. Process according to claim 1, wherein in said process a molar ratio between said compound with formula (2) and said organic peracid is between 0.25 and 10, preferably between 0.8 and 1.2.

11. Process according to claim 1, wherein in said process the concentration by weight of the reagents in the solution is between 1% and 100%, preferably between 15% and 40%.

12. Process according to claim 1, wherein $R^1$ is hydrogen.

13. Process according to claim 1, wherein n is between 3 and 5.

14. Process according to claim 1, wherein n is 3, $R^1$ is hydrogen and $R^3$ is hydrogen.

* * * * *